United States Patent [19]

Lamberti

[11] 3,976,642

[45] Aug. 24, 1976

[54] SULFOSUCCINATE DERIVATIVES AS DETERGENT BUILDERS

[75] Inventor: Vincent Lamberti, Upper Saddle River, N.J.

[73] Assignee: Lever Brothers Company, New York, N.Y.

[22] Filed: May 19, 1975

[21] Appl. No.: 578,704

Related U.S. Application Data

[62] Division of Ser. No. 484,741, July 1, 1974, Pat. No. 3,922,271, which is a division of Ser. No. 394,613, Sept. 5, 1973, Pat. No. 3,925,375, which is a division of Ser. No. 156,933, June 25, 1971, abandoned.

[52] U.S. Cl. ............ 260/247.1 E; 260/513 R; 260/501.15; 260/501.19; 260/501.21
[51] Int. Cl.² ............ C07D 295/00; C07C 143/00
[58] Field of Search.......... 260/247.1 E, 513 B, 260/513 R, 501.15, 501.19, 501.21

[56] References Cited
UNITED STATES PATENTS 3,635,829   1/1972   Yang ............................ 260/513 R
3,706,771   12/1972  Kremers et al. .............. 260/346.8

*Primary Examiner*—James O. Thomas, Jr.
*Assistant Examiner*—Nicky Chan
*Attorney, Agent, or Firm*—Arnold Grant

[57] ABSTRACT

Novel salts of α-substituted-β-sulfosuccinic acids having the general formula:

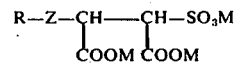

wherein R is hydrogen or an organic moiety, Z is selected from the group consisting of O, S, SO, $SO_2$, N and NO and M is an alkali metal, ammonium or substituted ammonium cations, useful as detergents and/or detergent builders and detergent compositions containing same.

5 Claims, No Drawings

SULFOSUCCINATE DERIVATIVES AS DETERGENT BUILDERS

This is a division of application Ser. No. 484,741, filed July 1, 1974, now U.S. Pat. No. 3,922,271, which in turn is a division of Ser. No. 394,613, filed Sept. 5, 1973, now U.S. Pat. No. 3,925,375, which is turn is a division of Ser. No. 156,933, filed June 25, 1971, now abandoned.

BACKGROUND OF THE INVENTION

Eutrophication is the process of excessive fertilization of aquatic plants through enrichment of waters with nutrients, such as carbon, nitrogen, phosphorus, potassium, iron, trace metals and vitamins.

Although there is no present adequate proof, it has been postulated that the phosphorus-containing builders present in detergent compositions can be a factor in eutrophication. Therefore any substitutes which do not contain phosphorus may decrease to some extent the eutrophication.

It is therefore an object of the present invention to provide novel compounds which are useful as detergent builders. It is another object of the present invention to provide novel compounds which function as surface active agents and as detergent builders. It is still another object of the present invention to provide detergent compositions which are free of phosphorus-containing builders such as the alkali metal condensed phosphates.

DESCRIPTION OF THE INVENTION

It has now been discovered that the alkali metal ammonium and substituted ammonium salts of certain sulfoaliphatic dicarboxylic acids can serve as effective detergent builders in detergent compositions. The detergent builders and their acid forms employed in accordance with one embodiment of the present invention can be generally described as α-substituted-β-sulfosuccinic acids and salts thereof having the general formula:

Formula I

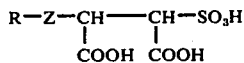

wherein Z is selected from the group consisting of O, S, SO and $SO_2$; R is selected from the group consisting of hydrogen, alkyl containing 1–30 carbon atoms, phenyl, carboxyl substituted and mono- di- or tri-alkyl substituted phenyl, wherein the alkyl group or groups contain 1–4 carbon atoms; sulfo- and carboxy-alkyl, wherein the alkyl moiety contains 1–4carbon atoms; and R'Z(CH$_2$CH$_2$O)n-CH$_2$CH$_2$-, wherein R' is H or alkyl containing 1–24 carbon atoms; Z is as above; and n is 0 or an integer of from 1–15 and the alkali metal, ammonium and substituted ammonium salts thereof.

Thus, specific compounds and classes of compounds embraced by the generic formula above include:

α-hydroxy-β-sulfosuccinic acids
α-alkoxy-β-sulfosuccinic acids
α-phenoxy-β-sulfosuccinic acids
α-carboxyphenoxy-β-sulfosuccinic acids
α-alkylphenoxy-β-sulfosuccinic acids
α-carboxyalkoxy-β-sulfosuccinic acids
α-sulfoalkoxy-β-sulfosuccinic acids
α-alkoxyethoxy-β-sulfosuccinic acids
α-alkoxypolyethyleneoxyethoxy-β-sulfosuccinic acids
α-hydroxyalkoxy-β-sulfosuccinic acids;

the alkali metal, ammonium and substituted ammonium salts thereof; and the thio, sulfinyl and sulfonyl analogs of all the foregoing compounds wherein the oxygen group attached to the α-carbon of the succinic acid or succinate moiety is replaced by —S—, —S— or —SO$_2$—, respectively, and/or wherein the cases of the α-alkoxyethoxy compounds and the α-alkoxypolyethyleneoxyethoxy compounds the oxygen attached to the alkyl group (R') is replaced by —S—, —SO— or —SO$_2$—.

In accordance with another embodiment of the present invention are the nitrogen containing α-substituted-β-sulfosuccinic acids and salts thereof having the following general formula:

Formula II

wherein at least one of $R_1$ and $R_2$ is hydrogen, $C_1$ to $C_{20}$ alkyl, $C_1$ to $C_4$ hydroxyalkyl, carboxymethyl, carboxyethyl, sulfomethyl and sulfoethyl, or $R_1$ and $R_2$ may be joined to form a morpholinyl moiety; with the proviso that both $R_1$ and $R_2$ may not at the same time be hydrogen.

Thus, broadly the compounds of Formula I differ from the compounds of Formula II only in the atom represented by Z.

Representative compounds and classes of compounds embraced by generic Formula II above include:

α-alkylamino-β-sulfosuccinic acids such as α-methylamino, α-propylamino, α-octylamino and α-laurylamino-β-sulfosuccinic acid;

α-dialkylamino-β-sulfosuccinic acids such as α-dimethylamino, α-ethylmethylamino, α-methylhexylamino and α-dioctylamino-β-sulfosuccinic acid;

α-hydroxyalkyl-β-sulfosuccinic acids such as α-hydroxyethylamino, α-hydroxybutylamino and α-bis(-hydroxyethyl)amino-β-sulfosuccinic acid;

α-carboxyalkylamino-β-sulfosuccinic acids such as α-carboxymethylamino, α-carboxyethylamino-β-sulfosuccinic acid and the corresponding sulfo analogs;

α-morpholinyl-β-sulfosuccinic acid; and the mono or poly salts thereof.

In accordance with still another embodiment of the present invention are the amine oxide derivatives of Formula II, wherein the nitrogen is a tertiary atom, corresponding to the following general formula:

Formula III

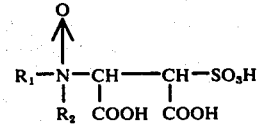

wherein $R_1$ and $R_2$ are as is designated in Formula II with the proviso that neither $R_1$ nor $R_2$ can be hydrogen.

As will be appreciated by those skilled in the art, the compounds of the invention contain at least two asymmetric carbon atoms and therefore can exist in several optically active forms as well as optically inactive mixtures (racemates). For purposes of this invention, the compounds as defined are intended to include all of the stereoisomeric forms and mixtures thereof.

In addition to the detergent building properties exhibited by the entire class of compounds described above, certain select members also exhibit properties which make them useful as wetting and foaming agents and thus constitute a class of novel surface active agents. For example, the $\alpha$-alkoxy-$\beta$-sulfosuccinic acids and the thio analogs, containing from about 1–8 carbons, preferably from about 1 to about 4 carbon atoms, exhibit excellent detergent building properties whereas the higher homologs containing from about 9–30 and more preferably 9–24 carbon atoms in the alkyl chain, additionally exhibit wetting, foaming and detergency properties.

Similarly, the $\alpha$-alkoxyethoxy and $\alpha$-alkoxypolyethyleneoxyethoxy-$\beta$-sulfosuccinic acid compounds containing from about 9–30 and preferably about 9–24 carbon atoms in the alkoxy moiety are also useful as wetting agents, foaming agents and detergents as well as detergent builders.

Although the builders of the present invention may be utilized as the free acid provided sufficient alkaline additives are included in the detergent composition to convert the acid forms in situ to the normal salt forms, the alkali metal, ammonium and substituted ammonium salts of the $\alpha$-substituted-$\beta$-sulfosuccinic acids are preferred. Included in the substituted ammonium salts that can be employed are the monoethanolammonium, diethanolammonium, triethanolammonium, methylammonium, dimethylammonium, trimethylammonium, tetramethylammonium, morpholinium, N-methylmonoethanolammonium and N-ethylmonoethanolammonium salts and mixtures thereof.

The utility of the compounds of the present invention is not only reflected in terms of excellent building and biodegradability properties but also in low cost of preparation, since they are prepared from readily available and inexpensive materials. For example, the compounds contemplated in this invention are derived from sulfomaleic anhydride and readily available alcohols, thiols, hydroxy acids and amines.

More specifically, the compounds contemplated in this invention are reaction products derived at least in part from sulfomaleic acid or sufomaleic anhydride with compounds having an active hydrogen atom.

Compounds having an active hydrogen and suitable for use in preparing the builders of the present invention are mono- di- or polyhydric alcohols and mono- di- or polyhydroxy acids and their sulfur-containing analogs. Suitable examples of the aforementioned monohydric alcohols include alkoxyalkanols such as methoxyethanol and the linear primary and secondary alcohols containing up to 30 carbon atoms and their thio analogs; aromatic alcohols particularly the carbocyclic mono- and bicyclic aromatic alcohols, such as naphthols and phenols and the mono- di- or tri- $C_1$-$C_4$ alkyl ring substituted derivatives thereof. Suitable examples of dihydric alcohols include the glycols such as ethylene glycol, propylene glycol, butylene glycol, trimethylene glycol, tetramethylene glycol, pentamethylene glycol, hexamethylene glycol, heptamethylene glycol, long chain 1,2-diols containing from 8–30 carbon atoms and aromatic carbocyclic glycols such as phenylethylene glycol. Similarly, suitable polyhydric alcohols include glycerol, pentaerythritol, hexanetriol, sugars and their thio analogs.

In addition to the alcohols, the hydroxy carboxylic and sulfonic acids (in their ester and acid/salt forms, respectively) may also react with sulfomaleic anhydride and sulfomaleic acid. These include glycolic, lactic, glyceric, hydroxypropionic, salicylic and mercapto acetic acid, hydroxymethanesulfonic acid and hydroxyethanesulfonic acid.

Still another important class of compounds containing active hydrogens are ethylene oxide adducts of $C_1$ to $C_{30}$ primary and secondary alcohols with 1–15 moles of ethylene oxide.

In general, the $\alpha$-substituted-$\beta$-sulfosuccinate salts, wherein the $\alpha$-substituent is joined to the $\alpha$-carbon atom of the sulfosuccinate moiety by an O or S linkage, may be prepared by heating at a temperature of from about 25° to 120°C, and preferably 60° to 100°C, sulfomaleic anhydride with a compound having an active hydrogen followed by further treatment with an alkali metal hydroxide. The desired $\alpha$-oxy or $\alpha$-thio-$\beta$-sulfosuccinate may then be recovered and purified using conventional techniques.

The $\alpha$-substituted-$\beta$-sulfosuccinate salts wherein the $\alpha$-substituent is joined to the $\alpha$-carbon atom of the sulfosuccinate moiety by an SO or $SO_2$ linkage may be prepared by treating the appropriate $\alpha$-substituted thio-$\beta$-sulfosuccinate with hydrogen peroxide according to the methods described on pages 471–472 in the text, "Reagents for Organic Synthesis" by Fieser and Fieser, published by John Wiley & Sons, Inc., 1967, incorporated by reference herein.

The $\alpha$-substituted-$\beta$-sulfosuccinate salts wherein the $\alpha$-substituent is joined to the $\alpha$-carbon atom of the sulfosuccinate moiety by an amino function (Formula II) may be prepared by reacting an appropriately substituted or unsubstituted primary or secondary amine with alkali metal salts of sulfomaleic acid. Typical amines suitable for reaction to form the $\alpha$-substituted amino-$\beta$-sulfosuccinates include:
ethanolamine
diethanolamine
propanolamine
morpholine
N-methylethanolamine
glycine
alanine
N-methyl taurine
alkylamines containing 1–20 carbons in the alkyl chain,
  as well as other amines having a replaceable or active hydrogen and a basicity comparable to the aforementioned amines.

In particular the $\alpha$-amino substituted-$\beta$-sulfosuccinates derived from water-soluble amines may be prepared by reacting in aqueous solution without the aid of heat and those derived from water-insoluble amines (i.e., higher alkylamines) are reacted in a mixed solvent system such as ethanol/water or dioxane/water at temperatures ranging from about 25°C to about 80°C; isolation from the reaction medium, and purification if desired, being effected by conventional methods.

The compounds of Formula III may be prepared by reacting the tertiary amine compounds of Formula II with oxidizing agents such as hydrogen peroxide, peroxyacetic and peroxyformic acid in the manner described for oxidizing tertiary amines by Hoh et al., J. Am. Oil Chemists' Soc., 40, 268 (1963).

In preparing the sulfosuccinate salts from the free acid, the amount of base utilized will determine whether the mono- di- or tri-salt is obtained. For example, the use of one mole of base (i.e., sodium hydroxide) per mole of $\alpha$-hydroxy-$\beta$-sulfosuccinic acid yields the monosodium salt; the use of two moles of sodium hydroxide, the disodium salt and the use of three moles of sodium hydroxide, the trisodium salt. When R is carboxymethyl, carboxyethyl, sulfomethyl or sulfoethyl, a tetrasalt can also be obtained. Similarly, other bases, such as ammonium hydroxide and organic amines, may be utilized in the same manner to afford the type of salt desired.

According to the present invention, excellent cleaning results can be obtained by using the builders described above with a wide range of detergent surface active materials and mixtures thereof in any of the usual physical forms for such compositions such as powders, beads, flakes, bars, tablets, noodles, liquids and the like. The builders can be used singularly, in combination with each other as the sole builder in the detergent composition or in combination with other wellknown detergent builders such as sodium nitrilotriacetate, sodium ethylenediaminetetraacetate, sodium tripolyphosphate, trisodium orthophosphate, sodium and potassium pyrophosphate, sodium polyacrylate, disodium oxydiacetate, trisodium citrate, trisodium carboxymethyloxysuccinate, salts of oxidized starches and sodium or potassium carbonate, as well as other conventional organic and inorganic builders.

When using the detergent compositions of the invention to wash clothes, the wash solutions should have a pH from about 7 to 12 and preferably from about 9 to 11 throughout the washing cycle. Therefore, the presence of an alkaline buffer in the detergent composition is usually desirable particularly when the soil to be removed from the clothes has a high content of acidic components. Suitable buffers include any of the common organic and/or inorganic buffers such as monoethanolamine, diethanolamine, triethanolamine, sodium and potassium silicates, sodium and potassium carbonates and bicarbonates and the like.

In the detergent compositions of the present invention, the only essential ingredients are the detergent surface active material and the builder. The weight percent of the builder present in the detergent composition will range from about 5 to about 90% and preferably from about 20 to about 60% and more preferably 35–50% by weight of the total weight of the composition. When expressed as a weight ratio of builder to surfactant, the builders used in the instant invention will generally be present in a ratio of about 1:10 to about 10:1, and preferably 2:1 to 5:1 depending on the end use or whether a heavy-duty or light-duty detergent is desired. When the builders are used in mechanical dishwashing compositions, the ratio of builder to surfactant is from about 10:1 to about 50:1.

The detergent surface active compounds which can be used within the compositions of this invention include anionic, nonionic, zwitterionic, ampholytic detergent compounds and mixtures thereof. These suitable substances are outlined at length below.

a. Anionic detergent compositions which can be used in the compositions of this invention include both soap and non-soap detergent compounds. Examples of suitable soaps are the sodium, potassium, ammonium and alkylolammonium salts of higher fatty acids ($C_{10}$–$C_{20}$). Particularly useful are the sodium or potassium salts of the mixtures of fatty acids derived from coconut oil and tallow, i.e., sodium or potassium tallow and coconut soap and tall oil. Examples of anionic organic non-soap detergent compounds are the water soluble salts, alkali metal salts of organic sulfuric reaction products having in their molecular structure an alkyl radical containing from about 8 to about 22 carbon atoms and a radical selected from the group consisting of sulfonic acid and sulfuric acid ester radicals. Important examples of the synthetic detergents which form a part of the compositions of the present invention are the sodium or potassium alkyl sulfates especially those obtained by sulfating the higher alcohols ($C_8$–$C_{18}$ carbon atoms) produced by reducing the glycerides of tallow or coconut oil; sodium or potassium alkyl benzensulfonates in which the alkyl group contains from about 9 to about 20 carbon atoms and in which the alkyl group is attached to the benzene ring in either the one position or at the secondary positions such as in LAS,* sodium p-(2-dodecyl-)benzenesulfonate, sodium p-(2-octadecyl)benzenesulfonates and sodium p-(3-dodecyl)benzenesulfonate; sodium alkyl glyceryl ether sulfonates, especially those ethers of the higher alcohols derived from tallow coconut oil and synthetic alcohols derived from petroleum; sodium coconut oil fatty acid monoglyceride sulfates and sulfonates; sodium or potassium salts of sulfuric acid esters and carboxymethylated derivatives of the reaction product of one mole of a higher fatty alcohol (e.g., tallow or coconut oil alcohols) and about 1 to 6 moles of ethylene oxide per molecule and in which the alkyl radicals contain about 9 to about 18 carbon atoms; the reaction product of fatty acids esterified with isethionic acid and neutralized with sodium hydroxide where, for example, the fatty acids are derived from coconut oil; sodium or potassium salts of fatty acid amides of methyl taurine in which the fatty acids, for example, are derived from coconut; alkane sulfonates such as those derived by reacting alpha-olefins containing 8 to 20 carbon atoms with sodium bisulfite and those derived by reacting paraffins with $SO_2$ and $Cl_2$ and then hydrolyzing with a base to produce a random sulfonate; alpha-olefin sulfonates such as those derived by reacting alpha-olefins with $SO_3$ and then neutralizing the reaction product; and others known in the art.

*Sodium linear secondary alkyl ($C_{10}$–$C_{15}$) benzene sulfonate.

b. Nonionic synthetic detergents may be broadly defined as compounds which do not ionize in water solution. For example, a well-known class of nonionic synthetic detergents is made available on the market under the trade name of "Pluronic." These compounds are formed by condensing ethylene oxide with an hydrophobic base formed by the condensation of propylene oxide with propylene glycol. The hydrophobic portion of the molecule which, of course, exhibits water insolubility has a molecular weight of from about 1,500 to 1,800. The addition of polyoxyethylene radicals to this hydrophobic portion tends to increase the water solubility of the molecule as a whole and the liquid character of the product is retained up to the point where polyoxyethylene content is about 50% of the total weight of the condensation product.

Other suitable nonionic synthetic detergents include:

1. The polyethylene oxide condensates of alkylphenols, e.g., the condensation products of alkylphenols having an alkyl group containing from about 6 to 12 carbon atoms in either a straight chain or branched chain configuration, with ethylene oxide, the said ethylene oxide being present in amounts equal to 5 to 25 moles of ethylene oxide per mole of alkylphenols. The alkyl substituent in such compounds may be derived from polymerized propylene, di-isobutylene, octene, dodecene, or nonene, for example.

2. Those derived from the condensation of ethylene oxide with the product resulting from the reaction of propylene oxide and ethylenediamine. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said hydrophobic base having a molecular weight of the order of 2,500 to 3,000 are satisfactory.

3. The condensation product of aliphatic alcohols, primary or secondary, having from 8 to 18 carbon atoms, in either straight chain or branched configuration, with ethylene oxide, e.g., a coconut alcohol-ethylene oxide condensate having from 6 to 30 moles of ethylene oxide per mole of coconut alcohol, the coconut alcohol fraction having from 10 to 14 carbon atoms; a $C_{11}-C_{15}$ random secondary alcohol derived from n-paraffins and condensed with 7 moles of ethylene oxide per mole of secondary alcohol.

4. Long chain tertiary amine oxides corresponding to the following general formula, $R_1R_2R_3N \rightarrow O$, wherein $R_1$ is an alkyl radical of from about 8 to 18 carbon atoms and $R_2$ and $R_3$ are each methyl, ethyl or hydroxy ethyl radicals. The arrow in the formula is a conventional representation of a semi-polar bond. Examples of amine oxides suitable for use in this invention include dimethyloctylamine oxide, dimethyldecylamine oxide, dimethyldodecylamine oxide, dimethyltetradecylamine oxide, dimethylhexadecylamine oxide and, N-bis(hydroxyethyl)dodecylamine oxide.

5. Long chain tertiary phosphine oxides corresponding to the following formula $RR'R''P \rightarrow O$, wherein R is an alkyl, alkenyl or monohydroxyalkyl radical ranging from 10 to 18 carbon atoms in chain length and $R'$ and $R''$ are each alkyl of monohydroxyalkyl groups containing from 1 to 3 carbon atoms. The arrow in the formula is a conventional representation of a semi-polar bond. Examples of suitable phosphine oxides are:
dimethyldodecylphosphine oxide,
dimethyltetradecylphosphine oxide,
ethylmethyltetradecylphosphine oxide,
cetyldimethylphosphine oxide,
dimethylstearylphosphine oxide,
cetylethylpropylphosphine oxide,
diethyldodecylphosphine oxide,
diethyltetradecylphosphine oxide,
bis(hydroxymethyl)dodecylphosphine oxide,
bis(2-hydroxyethyl)dodecylphosphine oxide,
2-hydroxypropylmethyltetradecylphosphine oxide,
dimethyloleylphosphine oxide, and
dimethyl-2-hydroxydodecylphosphine oxide.

6. Dialkyl sulfoxides corresponding to the following formula, $RR'S \rightarrow O$, wherein R is an alkyl, alkenyl, beta or gamma-monohydroxyalkyl radical or an alkyl or beta or gamma-monohydroxyalkyl radical containing one or two other oxygen atoms in the chain, the R groups ranging from 10 to 18 carbon atoms in chain length, and wherein $R'$ is methyl, ethyl or alkylol. Examples of suitable sulfoxide compounds are:
dodecyl methyl sulfoxide
tetradecyl methyl sulfoxide
3-hydroxytridecyl methyl sulfoxide
2-hydroxydodecyl methyl sulfoxide
3-hydroxy-4-decyloxybutyl methyl sulfoxide
3-hydroxy-4-dodecyloxybutyl methyl sulfoxide
2-hydroxy-3-decyloxypropyl methyl sulfoxide
2-hydroxy-3-dodecyloxypropyl methyl sulfoxide
dodecyl ethyl sulfoxide
2-hydroxydodecyl ethyl sulfoxide
dodecyl-2-hydroxy ethyl sulfoxide c. Ampholytic synthetic detergents can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group. Examples of compound falling within this definition are sodium-3-dodecylaminopropionate and sodium-3-dodecylaminopropanesulfonate and sodium N-2-hydroxydodecyl-N-methyl-taurate.

d. Zwitterionic synthetic detergents can be broadly described as derivatives of aliphatic quaternary ammonium compounds, sulfonium compounds and phosphonium compounds in which the aliphatic radical may be straight chain or branched and wherein one of the aliphatic substituents contains from about 8 to 18 carbon atoms and one contains an anionic water solubilizing group. Examples of compounds falling within this definition are 3-(N,N-dimethyl-N-hexadecylammonio)propane-1-sulfonate, 3-(N,N-dimethyl-N-hexadecylammonio)-2-hydroxypropane-1-sulfonate, 3-(dodecylmethylsulfonium) propane sulfonate, and 3-(cetylmethylphosphonium)ethane sulfonate.

Other materials which may be present in the detergent compositions of the invention in generally minor amounts are those conventionally present therein. Typical examples thereof include the well-known soil-suspending agents, hydrotropes, corrosion inhibitors, dyes, perfumes, fillers such as sodium sulfate, optical brighteners, perborates, bleaches, bleach activators, enzymes, suds boosters, suds depressants, germicides, fungicides, anti-tarnishing agents, cationic detergents, fabric softening agents and in the case of liquid compositions, opacifiers and organic solvents. The balance of the detergent compositions may be water or inert filler.

It has been discovered that when higher than normal levels of anionic, nonionic, ampholytic or zwitterionic surfactants are used with the sulfosuccinate derivative salts of this invention, the detergency of the formulation is significantly enhanced particularly at low formulation concentration (~0.1%) which are typically used by the U.S. housewife. For enhanced results the detergent formulation should contain surfactant levels of about 25% to about 45% by weight and the sulfosuccinate derivative salt levels of about 25% to about 75% by weight in the cases where the surfactants are anionic, ampholytic or zwitterionic. When the surfactant is a nonionic, enhanced detergency results are obtained when the level of said nonionic in the formulation is from about 15% to 30% by weight and the level of sulfosuccinate derivative salt is from about 25% to about 85% by weight.

In addition to their use in general household detergent compositions, the builders of the present invention find utility as boiler scale removers, stain removers and general chelating agents. When used at pH's of about 2 to about 5 as partially neutralized alkali metal, ammonium or substituted ammonium salts, especially in combination with wetting agents and surfactants, the compounds of the invention are excellent metal cleaning compounds.

Table 1 further illustrates the present invention. The detergent formulations set forth in the Table represent detergent compositions containing the builders of the present invention in combination with representative classes of surface active agents compared with control or standard phosphate built detergent compositions. The compositions were prepared by blending together the recited components in the proportions indicated, including an anticorrosive agent and buffer agent (sodium silicate). The compositions were then tested on vacuum cleaner dust soiled cloth for detergency or cleaning ability in the Terg-O-Tometer test; wherein washing conditions are as indicated and the results reported as detergency units. The average detergency units (DU) of the formulation is the final reflectance value of the washed cloth (average of 2 runs) minus the initial reflectance of the soiled cloth, the reflectances being obtained by measurement with a Gardner automatic color difference meter, Model AC-3.

EXAMPLE 1

Preparation of Trisodium α-Hydroxy-β-Sulfosuccinate

Sulfomaleic anhydride was prepared by heating a mixture of 1 mole of sulfur trioxide with 1 mole of maleic anhydride first at 60°C until the exothermic reaction subsided and then at 100°–110°C for 3 hours. Forty-five gm of sulfomaleic anhydride product was then mixed with 45 gm of ice and the resulting solution extracted 25 times with 50 ml portions of ether to remove maleic acid. A 20 ml portion of the resulting aqueous phase was collected, adjusted to pH = 11 with calcium hydroxide and refluxed for 4 hours. NMR analysis indicated that all of the sulfomaleic acid had hydrated within the first hour of reflux. The reaction mixture was then passed through a column of cation exchange resin. A portion of the effluent was then neutralized to pH = 8.5 and evaporated to a white crystalline residue (19.2 gm), which contained 80.9% of trisodium α-hydroxy-β-sulfosuccinate as determined by NMR analysis (using $D_2O$ solvent and K biphthalate as an internal standard) and 10.4% water by Karl Fischer analysis.

TABLE I

| Component | % Composition | | | | | | | | | | | |
|---|---|---|---|---|---|---|---|---|---|---|---|---|
| α-hydroxy[a] | 50 | 50 | 50 | 50 | 50 | | | | | | | |
| α-(2-hydroxyethoxy)[a] | | | | | | 50 | 50 | | | | | |
| α-dodecyloxy[a] | | | | | | | | 50 | | | | |
| α-methoxy[a] | | | | | | | | | 50 | | | |
| α-carboxymethoxy[a] | | | | | | | | | | 50 | | |
| α-dodecyloxyethoxy[a] | | | | | | | | | | | 50 | |
| α-dodecylthio[a] | | | | | | | | | | | | 50 |
| $Na_5P_3O_{10}$ | | | | | | | | | | | | |
| Sodium silicate ($SiO_2:Na_2O$ = 2.4:1) | 10 | 10 | 10 | 10 | 10 | 10 | 10 | 10 | 10 | 10 | 10 | 10 |
| Anionic[b] | 18 | | | | 18 | 36 | 18 | 18 | 18 | 18 | 18 | |
| Anionic[c] | | 18 | | | | | | | | | | |
| Nonionic[d] | | | 20 | | | | | | | | | |
| Ampholytic[e] | | | | 18 | | | | | | | | |
| Zwitterionic[f] | | | | | 18 | | | | | | | |
| Water | ← | | | | | bal | | | | | | → |
| Formulation Concentration, % | 0.2 | 0.2 | 0.2 | 0.2 | 0.2 | 0.2 | 0.1 | 0.2 | 0.2 | 0.2 | 0.2 | 0.2 |
| Detergency (DU's) | 24.6 | 24.4 | 26.5 | 23.1 | 25.6 | 26.1 | 24.7 | 27.1 | 23.0 | 24.2 | 15.4 | 22.3 |

| Component | Controls (% Composition) | | | | | | | | |
|---|---|---|---|---|---|---|---|---|---|
| α-hydroxy[a] | | | | | | | | | |
| α-(2-hydroxyethoxy)[a] | | | | | | | | | |
| α-dodecyloxy[a] | | | | | | | | | |
| α-methoxy[a] | | | | | | | | | |
| α-carboxymethoxy[a] | | | | | | | | | |
| α-dodecyloxyethoxy[a] | | | | | | | | | |
| α-dodecylthio[a] | | | | | | | | | |
| $Na_5P_3O_{10}$ | | | | | | | 50 | 50 | 50 |
| Sodium silicate ($SiO_2:Na_2O$ = 2.4:1) | 10 | 10 | 10 | 10 | 10 | 10 | 10 | 10 | 10 |
| Anionic[b] | 18 | 18 | | | | | | | |
| Anionic[c] | | | 18 | | | | 18 | | |
| Nonionic[d] | | | | 20 | | | | 20 | |
| Ampholytic[e] | | | | | 18 | | | | 18 |
| Zwitterionic[f] | | | | | | 18 | | | |
| Water | | | | | bal | | | | |
| Formulation Concentration, % | 0.1 | 0.2 | 0.2 | 0.2 | 0.2 | 0.2 | 0.2 | 0.2 | 0.2 |
| Detergency (DU's) | 4.8 | 6.4 | 16.1 | 19.9 | 18.8 | 20.1 | 28.7 | 29.4 | 28.5 |

[a]Sodium salts of α-substituted-β-sulfosuccinate
[b]Sodium linear secondary alkyl ($C_{10}$–$C_{15}$)benzene sulfonate
[c]Sodium $C_{15}$–$C_{18}$ α-olefin sulfonate
[d]$C_{11}$–$C_{15}$ linear secondary alcohols ethoxylated with 7 moles ethylene oxide/mole alcohol
[e]$C_{14}$–$C_{18}$ HAMT (sodium hydroxyalkyl N-methyl taurate)
[f]Sulfobetaine DCH (cocodimethylsulfopropyl betaine)
Washing conditions - 180 ppm (2:1 $Ca^{++}$/$Mg^{++}$); 120°F; pH 10

EXAMPLE 2

α-Thiosubstituted-β-Sulfosuccinates

The procedure of Example 1 is repeated except that in place of Ca(OH)$_2$ the pH is adjusted to 8.6 with NaOH. Then, an aqueous solution containing excess sodium hydrosulfide, sodium methyl mercaptide or sodium ethyl mercaptide is added and the resulting solution allowed to stand overnight. The reaction mixture is then passed through a column of cation exchange resin and the effluent evaporated to low volume. The pH is then adjusted to 8.5 with sodium hydroxide and the solution evaporated to dryness. In this way, there is afforded respectively:
trisodium α-mercapto-β-sulfosuccinate
trisodium α-methylthio-β-sulfosuccinate
trisodium α-ethylthio-β-sulfosuccinate

EXAMPLE 3

Preparation of Trisodium α-Methoxy-β-Sulfosuccinate

Sulfomaleic anhydride, 3.9 gm, was dissolved in 25 ml of methanol and refluxed for 5 hours. Then, 24 gm of 25% sodium methoxide in methanol was added and the solution was refluxed for 2 hours. The methanol was then evaporated and the residue was dissolved in 100 ml of water and heated for 1 hour at 80°C. The solution was then decolorized with 5 gm of charcoal, filtered and evaporated. The crude residue of trisodium α-methoxy-β-sulfosuccinate was purified by trituration with acetic acid and then filtered, washed with acetone and dried.

α-ethoxy-β-sulfosuccinate may be prepared by substituting ethanol and sodium ethoxide in the procedure described above.

EXAMPLE 4

Preparation of Trisodium α-Dodecyloxy-β-Sulfosuccinate

Sulfomaleic anhydride (10 gm) is mixed with 80 gm (0.45 mole) of n-dodecanol and heated at 100°C for 14 hours. A solution of 7.04 gm of sodium hydroxide in 50 ml water is then added and the mixture heated at 60°C for 2 hours. The heated mixture is then extracted three times with 300 cc portions of acetone (at reflux) and the acetone insoluble fraction is then filtered, washed with additional acetone and dried to give 16.2 gm of the title compound (structure confirmed by NMR and ion exchange of a sample followed by titration with standard sodium hydroxide: neutralization equivalent: found 147.0, theory 149.3).

EXAMPLE 5

Preparation of Trisodium α-Dodecyloxyethoxy-β-Sulfosuccinate

Using the procedure of Example 4 and substituting 37 gm (0.32 mole) of 2-dodecyloxyethanol in place of the n-dodecanol there is obtained trisodium α-dodecyloxyethoxy-β-sulfosuccinate.

EXAMPLE 6–8

Using n-tetradecanol in place of n-dodecanol in the procedure of Example 4 and carrying out the hydrolysis step with 10% excess aqueous sodium hydroxide at 80°C for 4 hours instead of 60°C for 2 hours, there is obtained trisodium α-tetradecyloxy-β-sulfosuccinate (Example 6). Similarly, using n-hexadecanol in place of n-dodecanol, there is obtained trisodium α-hexadecyloxy-β-sulfosuccinate (Example 7); using n-octadecanol, there is obtained trisodium α-octadecyloxy-β-sulfosuccinate (Example 8).

EXAMPLE 9

Preparation of Trisodium α-Hydroxyethoxy-β-Sulfosuccinate

Sulfomaleic anhydride (20 gm) is mixed with 37.2 gm (0.6 mole) of ethylene glycol and heated at 80°C for 4 hours. A solution of 16 gm (0.4 mole) of sodium hydroxide in 75 ml of water is then added and the mixture heated at 80°C for 4 hours. The mixture is then mixed with acetone to precipitate trisodium α-hydroxyethoxy-β-sulfosuccinate, which is purified by repeated extractions with hot acetone to remove all ethylene glycol and water followed by filtration and drying in an oven.

EXAMPLE 10

Preparation of the Tetrasodium salt of α-Carboxymethyloxy-β-Sulfosuccinic Acid Sulfomaleic anhydride (19.4 gm) is heated to 60°C and combined with 76 gm of ethyl glycolate. After heating the mixture at 80°C for 5½ hours, there is added a solution of 45 gm of sodium hydroxide dissolved in 135 gm of water and heating is continued at 80° for an additional three hours. The mixture is then diluted with water and passed through a column of a cation exchange resin. The resulting eluent is then evaporated in vacuo to a low volume and the concentrate extracted repeatedly with acetone to remove glycolic acid and other impurities. The resulting extracted residue is then dissolved in water and the pH of the solution adjusted to 8.6 with dilute sodium hydroxide. Evaporation of the solution in vacuo and drying over P$_2$O$_5$ gives a residue of the tetrasodium salt of α-carboxymethyloxy-β-sulfosuccinic acid.

EXAMPLE 11

Preparation of Trisodium α-(2-Hydroxyethylamino)-β-Sulfosuccinate

Sulfomaleic anhydride (prepared from a 1/1 mole ratio of SO$_3$/maleic anhydride by heating the mixture at 100°–110°C for 3 hours; active content, 86%), 20.7 gm (0.1 mole), was added to 100 gm of ice. The resulting solution was kept at 10°–15°C and neutralized to pH = 8.6 by slowly adding 28.4 gm of 50% sodium hydroxide. Monoethanolamine, 6.1 gm (0.1 mole), was next added slowly and the temperature allowed to rise to room temperature. After standing overnight, the reaction mixture was poured into 800 ml of acetone. The solvent was then decanted from the resulting syrupy lower layer and the latter reprecipitated three times from water with fresh acetone. The residue was then dried in a dessicator over P$_2$O$_5$ to give 38.8 gm of an off-white, granular product containing approximately 88% trisodium α-(2-hydroxyethylamino)-β-sulfosuccinate by titration with perchloric acid. The structure was confirmed by NMR analysis.

The above method is satisfactory for reacting water-soluble amino compounds with sulfomaleic anhydride. For water insoluble amino compounds such as the higher alkyl amines, a mixed solvent system such as ethanol/water and dioxane/water is used together with temperatures in the range of 25°–80°C.

Table 2 indicates the reactants and procedure required to obtain other α-substituted-β-sulfosuccinate salts having the R and Z moieties set forth in Formula 1.

methylammonium, dimethylammonium, trimethylammonium, tetramethylammonium, morpholinium, N-methylmonoethanolammonium and N-ethylmonoethanolammonium salts thereof, wherein n is an integer from 1 to 15.

TABLE 2

| R | Z | Ex. | Reactants (Sulfomaleic Anhydride +) |
|---|---|---|---|
| H | O | 1 | Water |
| Alkyl ($C_1$-$C_2$) | O | 3 | $C_1$ or $C_2$ alcohol |
| Alkyl ($C_3$-$C_{30}$) | O | 4–8 | $C_3$-$C_{30}$ primary, secondary, or tertiary alcohol |
| Phenyl | O | 4–8 | Phenol |
| Carboxyphenyl | O | 10 | Methyl salicylate |
| Alkylphenyl | O | 4–8 | Alkylphenol |
| o, m, p methylphenyl | O | 4–8 | o, m, p cresol, carvacrol, thymol |
| HOOC—$CH_2$— | O | 10 | Ethyl glycolate |
| HOOC—$CH_2CH_2CH_2$— | O | 10 | Methyl-β-hydroxypropionate |
| $HO_3S$—$CH_2CH_2$— | O | 4 | Isethionic acid |
| $R'O(CH_2CH_2O)_n$—$CH_2CH_2$— | O | 4 | $R'O(CH_2CH_2O)_nCH_2CH_2OH$ |
| $HOCH_2CH_2OCH_2CH_2$— | O | 4 | $HOCH_2CH_2OCH_2CH_2OH$ |
| $HO(CH_2CH_2O)_3CH_2CH_2$— | O | 4 | $HO(CH_2CH_2O)_3CH_2CH_2OH$ |
| $HO(CH_2CH_2O)_{10}CH_2CH_2$— | O | 4 | $HO(CH_2CH_2O)_{10}CH_2CH_2OH$ |
| $HO(CH_2CH_2O)_{15}CH_2CH_2$— | O | 4 | $HO(CH_2CH_2O)_{15}CH_2CH_2OH$ |
| $CH_3CH_2O(CH_2CH_2O)_3CH_2CH_2$— | O | 4 | $CH_3CH_2O(CH_2CH_2O)_3CH_2CH_2OH$ |
| $CH_3(CH_2)_{10}O(CH_2CH_2O)_9CH_2CH_2$— | O | 4 | $CH_3(CH_2)_{10}O(CH_2CH_2O)_9CH_2CH_2OH$ |
| $CH_3(CH_2)_{20}O(CH_2CH_2O)_3CH_2CH_2$— | O | 4 | $CH_3(CH_2)_{20}O(CH_2CH_2O)_3CH_2CH_2OH$ |
| $CH_3CH_2S(CH_2CH_2O)_3CH_2CH_2$— | O | 4 | $CH_3CH_2S(CH_2CH_2O)_3CH_2CH_2OH$ |
| $CH_3CH_2S(CH_2CH_2O)_9CH_2CH_2$— | O | 4 | $CH_3CH_2S(CH_2CH_2O)_9CH_2CH_2OH$ |
| $HOCH_2CH_2$— | O | 9 | Ethylene glycol |
| $HOCH_2CH_2CH_2$— | O | 9 | Trimethylene glycol |
| $HOCH_2(CH_2)_4CH_2$— | O | 9 | Hexamethylene glycol |
| H | S | 2 | Sodium hydrosulfide |
| Alkyl ($C_1$-$C_2$) | S | 2 | Sodium ($C_1$-$C_2$) alkyl mercaptide |
| Alkyl ($C_3$-$C_{30}$) | S | 4–8 | $C_3$-$C_{30}$ alkylmercaptan |
| Phenyl | S | 4–8 | Thiophenol |
| Carboxyphenyl | S | 10 | Methyl 2-mercaptobenzoate |
| Alkylphenyl | S | 4–8 | Alkylthiophenol |
| HOOC—$CH_2$— | S | 10 | Ethyl mercaptoacetate |
| HOOC—$CH_2$—$CH_2$— | S | 10 | Methyl β-mercaptopropionate |
| $HO_3SCH_2CH_2$— | S | 4 | Mercaptoethanesulfonic acid |
| $R'O(CH_2CH_2O)_nCH_2CH_2$— | S | 4 | $RO(CH_2CH_2O)_nCH_2CH_2SH$ |
| $HOCH_2CH_2OCH_2CH_2$— | S | 2 | $HOCH_2CH_2OCH_2CH_2SNa$ |
| $HO(CH_2CH_2O)_3CH_2CH_2$— | S | 2 | $HO(CH_2CH_2O)_3CH_2CH_2SNa$ |
| $HO(CH_2CH_2O)_{10}CH_2CH_2$— | S | 2 | $HO(CH_2CH_2O)_{10}CH_2CH_2SNa$ |
| $HO(CH_2CH_2O)_{15}CH_2CH_2$— | S | 2 | $HO(CH_2CH_2O)_{15}CH_2CH_2SNa$ |
| $CH_3CH_2O(CH_2CH_2O)_3CH_2CH_2$— | S | 4 | $CH_3CH_2O(CH_2CH_2O)_3CH_2CH_2SH$ |
| $CH_3(CH_2)_{11}O(CH_2CH_2O)_9CH_2CH_2$— | S | 4 | $CH_3(CH_2)_{11}((CH_2CH_2O)_9CH_2CH_2SH$ |
| $CH_3(CH_2)_{21}O(CH_2CH_2O)_3CH_2CH_2$— | S | 4 | $CH_3(CH_2)_{21}O(CH_2CH_2O)_3CH_2CH_2SH$ |
| $CH_3CH_2S(CH_2CH_2O)_3CH_2CH_2$— | S | 4 | $CH_3CH_2S(CH_2CH_2O)_3CH_2CH_2SH$ |
| $CH_3CH_2S(CH_2CH_2O)_9CH_2CH_2$— | S | 4 | $CH_3CH_2S(CH_2CH_2O)_9CH_2CH_2SH$ |
| $HOCH_2CH_2$— | S | 2 | Sodium 2-hydroxyethylmercaptide |
| $HOCH_2CH_2CH_2$— | S | 2 | Sodium 3-hydroxypropylmercaptide |
| $HOCH_2(CH_2)_4CH_2$— | S | 2 | Sodium 6-hydroxyhexylmercaptide |
| Alkyl ($C_1$-$C_2$) | SO | 2 | $C_1$-$C_2$ alkylmercaptan[a] |
| Alkyl ($C_3$-$C_{30}$) | SO | 4–8 | $C_3$-$C_{30}$ alkylmercaptan[a] |
| Phenyl | SO | 4–8 | Thiophenol[a] |
| Carboxyphenol | SO | 10 | Methyl 2-mercaptobenzoate[a] |
| $C_1$-$C_4$ alkylphenyl | SO | 4–8 | Alkylthiophenol[a] |
| HOOC—$CH_2$— | SO | 10 | Ethylmercaptoacetate[a] |
| HOOC—$CH_2CH_2$— | SO | 10 | Methyl β-mercaptopropionate[a] |
| $R'O(CH_2CH_2O)_nCH_2CH_2$— | SO | 5 | $R'O(CH_2CH_2O)_nCH_2CH_2SH$[a] |
| $HOCH_2CH_2$— | SO | 2 | Sodium 2-hydroxyethylmercaptide |
| $HOCH_2CH_2CH_2$— | SO | 2 | Sodium 3-hydroxypropylmercaptide |
| $HOCH_2(CH_2)_4CH_2$ | SO | 2 | Sodium 6-hydroxyhexylmercaptide |
| $C_1$-$C_2$ alkyl | $SO_2$ | 2 | $C_1$-$C_2$ alkylmercaptan[b] |
| $C_3$-$C_{30}$ alkyl | $SO_2$ | 4–8 | $C_3$-$C_{30}$ alkylmercaptan[b] |
| Phenyl | $SO_2$ | 4–8 | Thiophenol[b] |
| Carboxyphenyl | $SO_2$ | 4–8 | Methyl 2-mercaptobenzoate[b] |
| HOOC—$CH_2$— | $SO_2$ | 10 | Ethyl mercaptoacetate[b] |
| HOOC—$CH_2CH_2CH_2$— | $SO_2$ | 10 | Methyl 2-mercaptobutyrate[b] |
| $R'O(CH_2CH_2O)_nCH_2CH_2$— | $SO_2$ | 5 | $R'O(CH_2CH_2O)_nCH_2CH_2SH$[b] |

[a]Followed by oxidation to sulfoxide according to Fieser reference.
[b]Followed by oxidation to sulfone according to Fieser reference.

What is claimed is:

1. An α-hydroxypolyethyleneoxy-β-sulfosuccinic acid having the general formula:

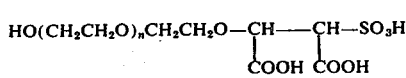

$HO(CH_2CH_2O)_nCH_2CH_2O$—$CH$—$CH$—$SO_3H$
                                            |         |
                                         COOH  COOH or the alkali metal, ammonium, monoethanolammonium, diethanolammonium, triethanolammonium, 2. The α-hydroxypolyethyleneoxy-β-sulfosuccinic acid or salts thereof of claim 1 wherein n is 1.

3. The α-hydroxypolyethyleneoxy-β-sulfosuccinic acid or salts thereof of claim 1 wherein n is 3.

4. The α-hydroxypolyethyleneoxy-β-sulfosuccinic acid or salts thereof of claim 1 wherein n is 10.

5. The α-hydroxypolyethyleneoxy-β-sulfosuccinic acid or salts thereof of claim 1 wherein n is 15.